United States Patent [19]

Dolgen

[11] 4,049,134
[45] Sept. 20, 1977

[54] MOVABLE LADLE IN A PRESSURIZED CONDUCT FOR TRANSPORTING SPECIMENS TO A COMBUSTION CHAMBER

[75] Inventor: Igor E. Dolgen, Monroe, Conn.

[73] Assignee: The Perkin-Elmer Corporation, Norwalk, Conn.

[21] Appl. No.: 654,426

[22] Filed: Feb. 2, 1976

[51] Int. Cl.² .................. B65G 65/30; G01N 1/00
[52] U.S. Cl. .................. 214/29; 73/190 R; 73/422 GC; 214/17 CC
[58] Field of Search ........... 214/17 B, 17 C, 17 CC, 214/34, 17 BC, 29; 73/15, 15.4, 422 GC, 9, 190 R; 250/288

[56] References Cited

U.S. PATENT DOCUMENTS

| 3,428,197 | 2/1969 | Fischer et al. ............ 214/17 B |
| 3,498,107 | 3/1970 | Kim et al. ............ 73/422 GC X |
| 3,730,364 | 5/1973 | Nakamura et al. ............ 73/190 R X |
| 3,779,712 | 12/1973 | Calvert et al. ............ 214/17 CC X |

FOREIGN PATENT DOCUMENTS

| 463,142 | 11/1968 | Switzerland ............ 73/19 |
| 1,129,062 | 10/1968 | United Kingdom ............ 214/34 |
| 204,238 | 9/1923 | United Kingdom ............ 214/34 |
| 1,032,975 | 6/1966 | United Kingdom ............ 214/17 CC |

Primary Examiner—Robert J. Spar
Assistant Examiner—Carl Rowold
Attorney, Agent, or Firm—S. A. Giarratana; F. L. Masselle

[57] ABSTRACT

A compact, sealable ladle transport for conveying material from a supply to a chamber, such as a combustion chamber, consists of an elongated ladle member longitudinally moved in a conduit to the combustion chamber by a power driven flexible tape attached to the ladle at one end and having its other end moving out from or back into a storage housing at the end of the conduit. In one position of the ladle material from a supply magazine is loaded onto it; the ladle is then moved forward to carry the material into the combustion chamber. After combustion, as the ladle is drawn back from the chamber, a wiper blade pivotted in the conduit sweeps the combustion residue into a receiving cavity at the bottom of the conduit. A port and passage, with a valve therein, opens into the conduit to provide means for applying purge gas through the conduit and chamber, and generally for controlling the pressure and composition of the atmosphere therein.

6 Claims, 1 Drawing Figure

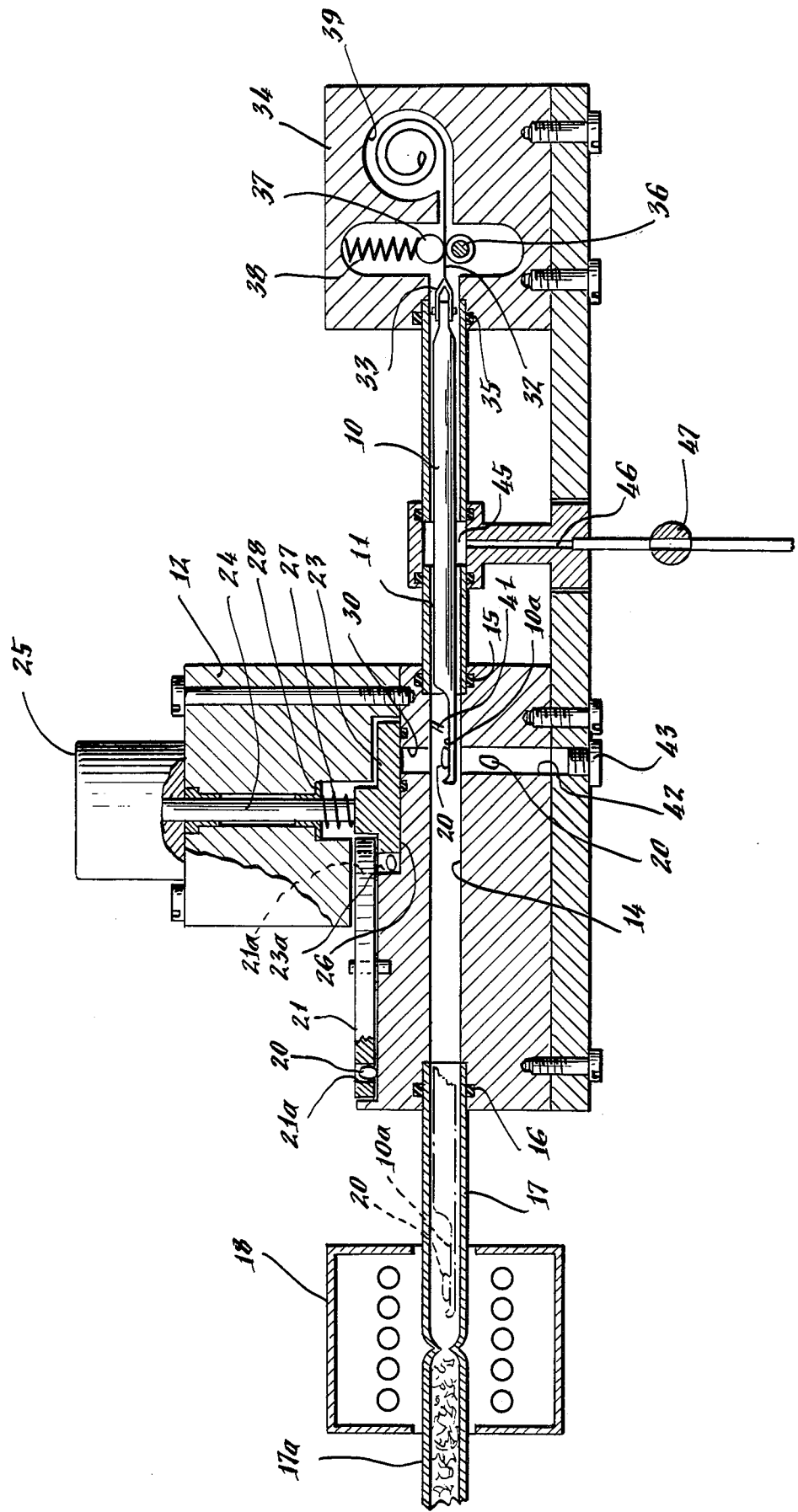

MOVABLE LADLE IN A PRESSURIZED CONDUCT FOR TRANSPORTING SPECIMENS TO A COMBUSTION CHAMBER

BACKGROUND OF THE INVENTION

The present invention relates to mechanisms for transporting small amounts of material from a supply to another location a short distance away. In particular, the invention is a ladle transport adapted for conveying small discrete amounts of material, in pellets or in capsules for example, from a supply to the combustion chamber of a combustion elemental analysis instrument in which material to be analyzed is burned and the combustion products analyzed to determine the quantitative presence of a particular element, eg. carbon, hydrogen; nitrogen. For convenience and clarity of understanding, the transport system of this invention is hereinafter described with particular reference to its adaptation for use with such a combustion elemental analytical instrument, but it will be understood that it would also be useful in other contexts.

In order to provide accurate analysis with the aforesaid types of analytical instruments the test material is customarily burned in a controlled atmosphere, eg. in pure oxygen, at a particular pressure so that means is provided for purging the combustion area between successive burnings and to have the combustion area sealed for providing and preserving the controlled atmosphere in which the combustion takes place. Provision is, of course, made for opening the chamber to receive the sample material to be burned and to be able to withdraw the ash residue after each burning. It is also desirable to be able to feed successive samples of test materials from a magazine supply into the combustion chamber and to remove the ash after each burning by some sort of transport mechanism that can be sealed from the outside, but without having to purge the interior after each burning and removal of the ash from the combustion chamber.

At present, in one known type of combustion analysis instrument, material to be analyzed is loaded into a platinum capsule which is then placed in a ladle boat. The end of a transfer tube is opened and the loaded boat is inserted. The tube is closed and a purge gas is flowed through the system to eliminate contaminants entering when the tube is opened, then the loaded boat is moved through the transfer tube to the combustion chamber by a magnet moved manually along the outside of the tube. After combustion, the boat with the capsule containing ash is magnetically withdrawn from the combustion chamber and back to the end of the tube which is opened for the first capsule containing ash to be removed from the boat and replaced by a new capsule containing new sample material. Due to the foregoing manual loading and feeding and having to purge the system for each load, the procedure is cumbersome and severely limits the time required for a series of analyses. Automatic loading systems have been proposed in which some sort of mechanical transport mechanism, adapted for automated sequential operation is employed, but in previously known mechanical systems the mechanisms for carrying capsules from a magazine to the cmbustion chamber and then to a residue receiving and holding tube or cavity are rather complex and take up a disproportionate amount of space.

It, is therefore, an object of the present invention to provide a mechanical transport system for the above purpose, and in general, for transporting discrete samples from a magazine supply a short distance and then back to be deposited in residue receiving recepticle, that is compact, that is adapted to be sealed, that is mechanically simple, and that is adapted to be operated sequentially by automated controls.

BRIEF DESCRIPTION OF THE INVENTION

In the compact sealable ladle transport of this invention, the ladle, which is an elongated member with a spoon portion at its front end, is slideable in a conduit which is connected to open into a chamber, such as the combustion chamber of a combustion elemental analytical instrument. The ladle member is moved in the conduit between a position in which material from a sample magazine is deposited in the spoon portion and a position in which the spoon portion is in the chamber by a driven flexible tape connected to the rear end of the ladle member and extending back into a housing. The tape is driven forward and back, to move the ladle member correspondingly, by a driver roller and idler roller pair between which the tape is gripped; when the tape is driven rearward, its rearward end portion coils up on itself in a cylindrical storage chamber in a housing at the rear of the conduit.

When the ladle member is drawn back from the chamber the residue of material in the spoon portion is swept out over the front end to fall into a residue receiving cavity in the bottom of the conduit by a wiper blade that is pivotted in the upper side of the conduit to ride over the top of the ladle member and then down into the spoon portion while the spoon portion moves back under the wiper.

A port and passage opening into the conduit with a valve is provided for feeding a gas, such as oxygen, in under pressure for maintaining a positive pressure in the conduit to keep contaminants out. Since successive test materials are located and fed into the combustion chamber from a self contained magazine without having to open the system to the atmosphere the necessity for purging the system after each new sample is placed in the transfer tube is eliminated and the whole operation is simpler, faster and more economical than with previously known loading and transport systems.

DESCRIPTION OF THE DRAWINGS

The ladle transport of this invention is described in detail below with reference to a preferred embodiment as illustrated in the sole drawing which is a longitudinal cross section through the transport, and through a furnace associated therewith.

DETAILED DESCRIPTION OF THE INVENTION

Referring to the drawing, a ladle transport in accordance with this invention includes an elongated ladle member 10 slideable in a main conduit 11. The forward (left hand) end of the conduit 11 is connected into a sample-material supply magazine housing 12, being connected in axial relation with the rear (right-hand) end of a passage 14 through the housing 12 by a sealed connection provided by an O-ring 15. The forward end of the housing passage 14 connects through a sealed connection provided by an O-ring 16 to a chamber that in the embodiment illustrated, is the combustion tube 17 of a combustion elemental analyzer instrument of which only the combustion tube 17 and a furnace portion 18 are shown.

In such a combustion analysis instrument, a sample of material to be analyzed is inserted in the combustion tube 17 to a point therein that is within the furnace portion 18 into which the tube 17 extends. In operation, with a sample of material in the portion of the tube 17 that is within the furnace portion 18, the tube 17 is purged if necessary to eliminate contaminants, by flowing a purge gas through it (suitably ports and valves being provided for this purpose) and the tube is filled with a gas that provides the controlled atmosphere in which the material is to be burned for the analysis. For example, for testing for carbon, hydrogen, or nitrogen, the test material will be burned in an oxygen atmosphere.

As the test material burns the gaseous combustion products are drawn into the analysis portion (not shown) of the instrument through a combustion tube extension 17a which extends from the tube 17, out through the opposite side (left) of the furnace portion. Thereafter, the solid residue of the combustion are withdrawn from the furnace portion 18, back through the combustion tube 17.

As noted above, the ladle transport of this invention is particularly adapted to provide a compact mechanically simple system for inserting test samples in the combustion tube or chamber of instruments of the foregoing type, and for removing solid combustion residue therefrom. For this purpose, the forward end of the ladle member 10 has a spoon portion 10a into which a pellet 20 of material to be tested is deposited from a supply of such pellets contained in a magazine which, in the embodiment illustrated, is a rotatable magazine drum 21 having a plurality of open-ended pockets 21a into each of which a pellets 20 is loaded. Motor means (not shown) may be provided for rotating the magazine drum 21.

The sample material to be analyzed will normally be provided in the form of pellets, in order to have successive samples all of the same weight or volume. In one usual form, the material to be analyzed is loaded into the platinum capsules which among other things are not consumed by the burning and contain the solid combustion residue for convenient withdrawal from the furnace.

The magazine drum 21 is mounted on a surface of the housing 12 in a position for one edge portion to overlap an edge portion of a loading disc 23 which is also rotatably supported in the magazine housing 12 and which has a plurality of open-ended pellet receiving pockets 23a therethrough. The loading disc 23 is rotatably supported in the magazine housing 12 by being fixed on a shaft 24 which is driven by a motor 25, for rotating the disc. The motor 25, or separately operable motor means (not shown) may be connected (by means not shown) to rotate the magazine drum 21. The bottom surface of the disc is held down against a surface 26 in the housing 12 by a spring 27 which is disposed around the shaft 24 and constrained between the top of the disc and a shoulder 28 in the housing 12. The pockets 23a of the loading disc 23 are arranged in a circle concentrically around the center thereof so that each becomes aligned to receive a pellet 20 from the magazine drum 21 at one rotational position of the disc 23; at another rotational position of the disc 23, each of the pockets 23a becomes registered with an aperture 30 that extends down through the housing surface 26 to open into the passage 14 so that pellet 20 to drops down from each pocket 23a through the aperture 30 to be received in the ladle spoon portion 10a positioned below the aperture 30. The motor (not shown) for rotating magazine drum 21 will thus be actuated when desired for example, as part of a sequence of programmed steps in the automated operation of the instrument to which the ladle transport of this invention is connected for transferring successive pellets from pockets 21a of the magazine drum 21 and depositing them in the ladle spoon portion 10a for the start of an operative cycle of the instrument.

The ladle member 10 is moved back and forth in the conduit 11, passage 14 and combustion tube 17, between the position (shown in full lines) in which the ladle spoon portion 10a receives a pellet 20 from the magazine and the forward position (indicated in dash line) in which the spoon portion 10a, and a pellet 20 therein, are within the furnace 18, by means of a driven flexible tape 32 attached to the rearward end of the ladle member 10 as by a clevis type connection 33.

The tape 32 is moved out of and back into a storage housing 34 which is sealed to the rear end of the conduit 11 by an O-ring 35, for correspondingly moving the ladle member by driven means within the housing 34 consisting of a driver roller 36 and a cooperating idler roller 37 between which the tape passes. The idler roller 37 is urged toward the driver roller 36 by a spring 38 to provide the requisite frictional engagement with the tape. As the rearward end of the tape 32 is driven back into the housing 34, it is coiled by the cylindrical configuration of a storage chamber 39 within the housing 34 in which the rear end of the tape is received. Thus the storage space required for a tape of sufficient length to drive the ladle member 10 from the magazine of pellets 20 to the furnace 18 is minimized.

The driver roller 36 may be driven by suitable means (not shown) of any well known conventional type including a motor which, like the disc drive motor 25, may be actuated in an automated sequence for moving the ladle member to its different positions as required for a cycle of operation of the instrument.

When the ladle member 10 is drawn back from the furnace 18 with solid combustion residue, or a capsule containing such residue, in its spoon portion 10a, the residue is swept out over the front of the spoon portion by a wiper blade 41 that is pivotally mounted in the passage 14, in the magazine housing 12, to pivot down into the passage 14. The wiper blade 41 is provided sufficient clearance to ride over the top of the ladle member as the ladle member moves forward under it. Then when the ladle member is drawn back under the wiper blade, the wiper blade rides down into the spoon portion 10a. Any residue thus swept out of the spoon portion by the wiper blade falls down into a residue receiving cavity 42 that is in the lower portion of the magazine housing 12 to open into the bottom of the passage 14 at a location to receive such residue. The bottom of the residue receiving cavity is closed by a cap 43 which seals it from the surrounding atmosphere, but which is removable for cleaning out accumulated residue when the instrument is not in its combustion cycle.

The main conduit 11 is also provided with a port 45 opening into it from a conduit 46 which has a valve 47 therein for closing it or for opening it to a source of gas, such as oxygen under pressure.

In operation, the instrument to which the ladle transport of this invention is operatively connected and the interior of the ladle transport are first purged or flushed by forcing air or a gas under pressure through it. Gas applied through conduit 46 and valve 47 may be used for this purpose. When the purging is completed, the valve 47 is opened sufficiently for supplying a gas, such as oxygen, to the conduit under pressure that is at least sufficient to create a positive pressure, relative to the atmosphere pressure exteriorly of the instrument, so as to prevent air or contaminants from entering the system.

Next, the ladle member is positioned with its spoon portion 10a in line with the aperture 30 and the loading disc 23 is rotated to bring one of its pockets 23a containing a pellet 20 in register with the aperture 30 so that the pellet drops down therethrough and into the ladle spoon portion 10a. The ladle member 10 is then moved forward by the driven tape 32 to bring the spoon portion 10a and pellet 20 therein into the furnace 18 for the combustion. After combustion and after the gaseous combustion products have been withdrawn into the analytical portion of the instrument, through combustion tube extension 17a, the analytical portion of the instrument is shut off from the furnace portion by suitable valve means (not shown). Then the ladle member 10 is drawn back from the furnace at least to the point at which the wiper blade 41 operates to sweep residue out of the spoon portion 10a into the residue receiving cavity 42.

It will thus be seen that the tape driven ladle transport of this invention can be readily sealed from outside atmosphere, is adapted to feed a succession of pellets to the desired location from a magazine by mechanical means which may be operated automatically, and contains mechanism for such operation in a minimum of space.

What is claimed is:

1. A pressurized ladle transport for operation between supply and delivery locations, comprising:
   an elongated conduit connected at one end to the delivery location and having an aperture thereinto at the supply location;
   an elongated ladle slideably disposed within said conduit and having a spoon portion on the end thereof that is directed toward the delivery location;
   a housing connected to the other end of said conduit;
   a flexible tape connected to the other end of said ladle and extending into said housing, the length of said tape being sufficient to extend from within said housing when said spoon portion on said ladle is at the delivery location;
   means for driving said tape bidirectionally relative to said housing;
   means for storing said tape within said housing; and a source of gas connected to pressurize said conduit, said source being at a pressure greater than the atmosphere exterior to said conduit, said drive means being controllable to move said tape in positioning said ladle at either the supply or delivery locations with material being deposited on said spoon portion thereof through said aperture at the supply location and the environment within the ladle transport being uncontaminated by the exterior atmosphere due to the pressurization therein.

2. The ladle transport of claim 1 wherein the delivery location is a chamber; wherein said chamber, said housing, and said source of gas are connected to said conduit through o-ring seals; and wherein said conduit includes a second housing with said aperture being disposed therein, said second housing having a disc rotatably disposed thereon over said aperture, said disc having ports disposed therethrough in a circular pattern about the center thereof, each said port being aligned with said aperture at one rotational position of said disc and the material to be transported is placed in said ports for deposit on said spoon portion of said ladle when said ports become aligned with said aperture.

3. The ladle transport of claim 2 wherein a second disc is rotatably disposed on said second housing, said second disc having ports disposed therethrough in a circular pattern about the center thereof, each said port in said second disc being aligned over one port in said first disc at a rotational position of each disc and the material to be transported is placed in said ports of said second disc for deposit into said ports of said first disc when alignment exists therebetween.

4. The ladle transport of claim 1 wherein a second aperture is disposed into said conduit on the bottom side thereof and a wiper element is pivotally disposed within said conduit to sweep any material on said spoon portion of said ladle into said second aperture when said ladle is returned from the delivery location.

5. The ladle transport of claim 1 wherein said tape drive means includes a driver roller and an idler roller between which said tape is gripped due to the force of a spring on said idler roller.

6. The ladle transport of claim 1 wherein said tape storage means includes a cylindrical chamber in said housing, said cylindrical chamber having the longitudinal axis thereof aligned normal to the bidirectional movement of said tape, said tape being looped upon itself in a coil by said cylindrical chamber when moving into said housing.

* * * * *

UNITED STATES PATENT AND TRADEMARK OFFICE
CERTIFICATE OF CORRECTION

PATENT NO. : 4,049,134
DATED : September 20, 1977
INVENTOR(S) : Igor E. Dolgen

It is certified that error appears in the above-identified patent and that said Letters Patent are hereby corrected as shown below:

Column 3, line 19, after "portion" and before the period (.), insert --18--;

line 63, after "23", delete the semicolon (;) and insert in place thereof a period (.); and delete "at" and insert in place thereof --At--;

line 67, delete "to".

Column 4, line 1, after "motor", insert --25 and a motor--.

Column 5, line 33, delete "9n".

Signed and Sealed this

Twentieth Day of December 1977

[SEAL]

Attest:

RUTH C. MASON
Attesting Officer

LUTRELLE F. PARKER
Acting Commissioner of Patents and Trademarks